(12) United States Patent
Majeed et al.

(10) Patent No.: US 11,491,119 B2
(45) Date of Patent: Nov. 8, 2022

(54) CURCUMINOID COMPOSITION AND ITS THERAPEUTIC POTENTIAL IN MANAGING LUNG FIBROSIS

(71) Applicants: Muhammed Majeed, Bangalore (IN); Kalyanam Nagabhushanam, East Windsor, NJ (US); Lakshmi Mundkur, Bangalore (IN); Rajendran Ramanujam, Bangalore (IN)

(72) Inventors: Muhammed Majeed, Bangalore (IN); Kalyanam Nagabhushanam, East Windsor, NJ (US); Lakshmi Mundkur, Bangalore (IN); Rajendran Ramanujam, Bangalore (IN)

(73) Assignee: SAMI-SABINSA GROUP LIMITED, Bangalore (IN)

( * ) Notice: Subject to any disclaimer, the term of this patent is extended or adjusted under 35 U.S.C. 154(b) by 79 days.

(21) Appl. No.: 17/071,682

(22) Filed: Oct. 15, 2020

(65) Prior Publication Data
US 2021/0106544 A1    Apr. 15, 2021

Related U.S. Application Data

(60) Provisional application No. 62/915,068, filed on Oct. 15, 2019.

(51) Int. Cl.
| | |
|---|---|
| *A61K 31/12* | (2006.01) |
| *A61K 36/9066* | (2006.01) |
| *A61P 11/02* | (2006.01) |
| *A61P 1/16* | (2006.01) |
| *A61P 31/14* | (2006.01) |
| *A61P 11/00* | (2006.01) |
| *A61P 29/00* | (2006.01) |

(52) U.S. Cl.
CPC ................ *A61K 31/12* (2013.01); *A61P 1/16* (2018.01); *A61P 11/00* (2018.01); *A61P 29/00* (2018.01); *A61P 31/14* (2018.01)

(58) Field of Classification Search
CPC ...... A61K 31/12; A61K 36/9066; A61P 11/02
See application file for complete search history.

*Primary Examiner* — Marcos L Sznaidman
*Assistant Examiner* — Rayna Rodriguez (57) ABSTRACT

The present invention discloses a composition comprising 70%-80% w/w tetrahydrocurcuminoids, 10%-20% w/w hexahydrocurcuminoids and 5%-10% w/w octahydrocurcuminoids and its therapeutic application. More specifically, the present invention discloses the use of a composition comprising 70%-80% w/w tetrahydrocurcuminoids, 10%-20% w/w hexahydrocurcuminoids and 5%-10% w/w octahydrocurcuminoids in the therapeutic management of interstitial lung disease or lung fibrosis.

13 Claims, 9 Drawing Sheets
(2 of 9 Drawing Sheet(s) Filed in Color)
Specification includes a Sequence Listing.

CURCUMINOID COMPOSITION AND ITS THERAPEUTIC POTENTIAL IN MANAGING LUNG FIBROSIS

CROSS-REFERENCE TO RELATED APPLICATION

This is a non-provisional filing claiming priority from U.S. provisional application No. 62/915,068, filed on 15 Oct. 2019, the subject matter of which is incorporated herein by reference.

FILED OF INVENTION

The present invention relates to a curcuminoid composition and its therapeutic applications thereof. More specifically the invention relates to the composition comprising Tetrahydrocurcuminoids (THCs), Hexahydrocurcuminoids (HHCs) and Octahydrocurcuminoids (OHCs) and their potential in alleviating symptoms of lung fibrosis.

BACKGROUND OF THE INVENTION

Description of Prior Art

Pulmonary fibrosis also termed as interstitial pulmonary lung disease (ILD), is a general term that describes chronic lung disorders. It results due to a combination of inflammation and fibrosis of the lung parenchyma (Kalchiem-Dekel et al., Interstitial Lung Disease and Pulmonary Fibrosis: A Practical Approach for General Medicine Physicians with Focus on the Medical History, J Clin Med. 2018 December; 7(12): 476). The condition affects the lungs in three ways: 1) damaging the lung tissue, 2) inflammation of the interstitium and 3) Fibrosis in the interstitium and alveoli.

ILD results from a variety of environmental, avocational, occupational, or medication-related exposures, or from the systemic autoimmune or connective tissue diseases (CTD). Chemotherapeutic agents, anti-arrhythmic agents, certain psychiatric medications and some antibiotics (like ciprofloxacin) are also known to cause ILD. Certain infections like CMV, HIV, bacterial/fungal infections (pneumonia, histoplasmosis, and parasitic infections (like lung fluke worms) are also reported to cause lung fibrosis. (Ross M H & Murray J. Occupational respiratory disease in mining Occup Med (Lond). 2004, 54: 304-310; Camus et al, Drug-induced and iatrogenic infiltrative lung disease Clin Chest Med. 2004, 25: 479-519). The following prior art documents disclose the causes important pathological features of ILD.
  i) Kalchiem-Dekel et al., Interstitial Lung Disease and Pulmonary Fibrosis: A Practical Approach for General Medicine Physicians with Focus on the Medical History, J Clin Med. 2018 December; 7(12): 476
  ii) Raghu G, Brown K K. Interstitial lung disease: Clinical evaluation and keys to an accurate diagnosis. Clin Chest Med. 2004, 25: 409-419;
  iii) King T E Jr. Clinical advances in the diagnosis and therapy of the interstitial lung diseases. Am J Respir Crit Care Med. 2005, 172: 268-279.
  iv) Crystal et al., Interstitial lung disease: Current concepts of pathogenesis, staging and therapy, The American Journal of Medicine, Volume 70, Issue 3, March 1981, Pages 542-568
  v) Harrison et al., Structural Features of Interstitial Lung Disease in Systemic Sclerosis, Am Rev Respir Dis, 1991, 144(3 Pt 1):706-13.

The most common symptom of ILD is shortness of breath which worsens with the severity of the disease. ILD can cause multiple complications which include pulmonary hypertension, Respiratory failure and cur pulmonale (right side heart failure). The Pandemic of COVID-19 infection has affected the entire population of the world. One of the possible complications in COVID-19 is pulmonary fibrosis, which leads to chronic breathing difficulties, long-term disability and affects patients' quality of life. Clinical, radiographic, and autopsy reports of patients have shown pulmonary fibrosis, while existing fibrotic conditions could complicate infection by SARS-CoV-2 (Zumla et al., "Reducing mortality from 2019-nCoV: host-directed therapies should be an option," The Lancet, 2020, 395(10224): e35-e36; Ademola et al., Pulmonary Fibrosis in COVID-19 Survivors: Predictive Factors and Risk Reduction Strategies, Pulmonary Medicine, 2020, Article ID 6175964, 10 pages). Various mechanisms of lung injury in COVID-19 have been described, with both viral and immune-mediated mechanisms being implicated (Liu, et al., "Overlapping and discrete aspects of the pathology and pathogenesis of the emerging human pathogenic coronaviruses SARS-CoV, MERS-CoV, and 2019-nCoV," Journal of Medical Virology, vol. 92, no. 5, pp. 491-494, 2020) Further oxidative stress is a major factor increasing the severity of COVID-19, and anti oxidant supplementations are recommended in therapeutic strategies against COVID-19 (Derouiche S, Oxidative Stress Associated with SARS-Cov-2 (COVID-19) Increases the Severity of the Lung Disease—A Systematic Review. J Infect Dis Epidemiol, 2020, 6:121. doi.org/10.23937/2474-3658/1510121)

The treatment for ILD is dependent diagnosis and severity of the disease. The most common treatment methods include administration of antibiotics and corticosteroids. In some cases inhaled oxygen is also provided to reduce the hypoxia developed as a result of ILD. Drugs like azathioprine, N-acetylcysteine, Cyclophosphamide, Cyclosporine, Methotrexate, Nintedanib, Pirfenidone are also administered for the treatment of ILD. Advanced stages of ILD might have to treated by a lung transplant.

Since the redox imbalance is substantial in the ILD, treatment with antioxidants would also help in mitigating the disease condition (Day B J, Antioxidants as Potential Therapeutics for Lung Fibrosis, Antioxid Redox Signal. 2008: 10(2): 355-370). Natural molecules derived from medicinal plants are also reported to mitigate lung inflammation and associated diseases (Santana et al., Evidences of Herbal Medicine-Derived Natural Products Effects in Inflammatory Lung Diseases, Mediators Inflamm. 2016; 2016: 2348968). However, there still exists an industrial need for a natural plant based composition that is very effective in managing the symptoms of ILD.

The compounds obtained from *Curcuma* species, specifically curcuminoids, and their role in therapeutic management of various diseases and disorders are well documented. Recently metabolites of curcuminoids are garnering the much attention owing to their similar and superior efficacy over curcumin (Majeed et al., Reductive Metabolites of Curcuminoids, Nutriscience Publishers LLC, 2019). The pharmacological activities of reductive metabolites of curcumin such as tetrahydrocurcumin, as represented by STR #1, hexahydrocurcumin as represented by STR #2 and octahydrocurcumin as represented by STR #3 are yet to be proven and tapped for industrial application. The reductive metabolites also include tetrahydro-demethoxycurcumin (STR #4), tetrahydrobis-demethoxycurcumin (STR #5), hexahydro-demethoxycurcumin (STR #6), hexahydrobisdemethoxycurcumin (STR #7), octahydro-demethoxycurcumin (STR #8) and octahydrobis-demethoxycurcumin (STR #9).

These reductive metabolites of curcumin are commonly bio transformed by the reductive enzymes (Mimura et. al., U.S. Pat. No. 5,266,344; Pan et al., Biotransformation of curcumin through reduction and glucuronidation in mice, Drug Metab Dispos, 1999, 27(1):486-494). They are also identified in nature and isolated from different plant sources (Majeed et al., Reductive Metabolites of Curcuminoids, Nutriscience Publishers LLC, 2019). The present invention discloses a composition comprising metabolites of curcuminoids, specifically tetrahydrocurcumin, hexahydrocurcumin and octahydrocurcumin and its therapeutic potential in the management of lung fibrosis.

It is the principle object of the invention to disclose a composition comprising tetrahydrocurcumin, hexahydrocurcumin and octahydrocurcumin.

It is another object of the invention to disclose the use of a composition comprising tetrahydrocurcumin, hexahydrocurcumin and octahydrocurcumin in the therapeutic management of interstitial lung disease.

The present invention fulfils the abovementioned objects and provides further related advantages.

SUMMARY OF THE INVENTION

In a most preferred embodiment, the invention discloses a composition comprising 70%-80% w/w tetrahydrocurcuminoids, 10%-20% w/w hexahydrocurcuminoids and 5%-10% w/w octahydrocurcuminoids.

In another preferred embodiment, the invention discloses a method for the therapeutic management of interstitial lung disease in mammals, said method comprising step of administering a composition comprising 70%-80% w/w tetrahydrocurcuminoids, 10%-20% w/w hexahydrocurcuminoids and 5%-10% w/w octahydrocurcuminoids to mammals in need of such therapeutic management.

In another preferred embodiment, the invention discloses the use of a composition 70%-80% w/w tetrahydrocurcuminoids, 10%-20% w/w hexahydrocurcuminoids and 5%-10% w/w octahydrocurcuminoids in the therapeutic management of interstitial lung disease in mammals.

In another preferred embodiment, the invention discloses a method for the inhibiting mast cell degranulation in mammals, said method comprising step of bringing into contact mast cells with a composition comprising 70%-80% w/w tetrahydrocurcuminoids, 10%/6-20% w/w hexahydrocurcuminoids and 5%-10% w/w octahydrocurcuminoids to bring about inhibition in histamine and cytokine release.

In another preferred embodiment, the invention discloses the use of a composition comprising 70%-80% w/w tetrahydrocurcuminoids, 10%-20% w/w hexahydrocurcuminoids and 5%-10% w/w octahydrocurcuminoids in inhibiting mast cell degranulation in mammals.

Other features and advantages of the present invention will become apparent from the following more detailed description, which illustrate, by way of example, the principle of the invention.

BRIEF DESCRIPTION OF THE DRAWINGS

The patent or application file contains at least one drawing executed in color. Copies of this patent or patent application publication with color drawing(s) will be provided by the office upon request and payment of the necessary fee.

DETAILED DESCRIPTION OF PREFERRED EMBODIMENTS

In a most preferred embodiment, the invention discloses a composition comprising 70%-80% w/w tetrahydrocurcuminoids, 10%-20% w/w hexahydrocurcuminoids and 5%-10% w/w octahydrocurcuminoids. In a related aspect, the tetrahydrocurcuminoids comprise of tetrahydrocurcumin, tetrahydro-demethoxycurcumin and tetrahydrobisdemethoxycurcumin. In another related aspect, the hexahydrocurcuminoids further comprise of hexahydrocurcumin, hexahydro-demethoxycurcumin and hexahydrobisdemethoxycurcumin. In another related embodiment, the hexahydrocurcuminoids exist in racemic or as one of its two chiral (S or R) forms. In yet another preferred embodiment, octahydrocurcuminoids further comprise of octahydrocurcumin, octahydro-demethoxycurcumin and octahydrobisdemethoxycurcumin. In a further related embodiment the octahydrocurcuminoids exist in meso or dextrorotatory or levorotatory forms (All the forms exist within the present embodiment and are claimed to be part of the active forms). In a further related aspect, the composition further comprises of stabilizing agents, bioavailability enhancers and antioxidants, pharmaceutically or nutraceutically or cosmeceutically accepted excipients and enhancers.

In another preferred embodiment, the invention discloses a method for the therapeutic management of interstitial lung disease in mammals, said method comprising step of administering a composition comprising 70%-80% w/w tetrahydrocurcuminoids, 10%-20% w/w hexahydrocurcuminoids and 5%-10% w/w octahydrocurcuminoids to mammals in need of such therapeutic management. In a related aspect, the tetrahydrocurcuminoids comprise of tetrahydrocurcumin, tetrahydro-demethoxycurcumin and tetrahydrobisdemethoxycurcumin. In another related aspect, the hexahydrocurcuminoids further comprise of hexahydrocurcumin, hexahydro-demethoxycurcumin and hexahydrobisdemethoxycurcumin. In yet another preferred embodiment, octahydrocurcuminoids further comprise of octahydrocurcumin, octahydro-demethoxycurcumin and octahydrobisdemethoxycurcumin. In yet another related aspect, the therapeutic effect is brought about by decreasing collagen deposition, decreasing collagen 1A gene expression, reducing TGF-β levels, reducing oxidative stress and inflammation, reducing accumulation of Inflammatory cells in Bronchoalveolar lavage (BAL) fluids and inhibiting mast cell degranulation. In a further related aspect, the composition further comprises of stabilizing agents, bioavailability enhancers and antioxidants, pharmaceutically or nutraceutically or cosmeceutically accepted excipients and enhancers. In a preferred embodiment, the mammal is human.

In another preferred embodiment, the invention discloses the use of a composition 70%-80% w/w tetrahydrocurcuminoids, 10%-20% w/w hexahydrocurcuminoids and 5%-10% w/w octahydrocurcuminoids in the therapeutic management of interstitial lung disease in mammals. In a related aspect, the tetrahydrocurcuminoids comprise of tetrahydrocurcumin, tetrahydro-demethoxycurcumin and tetrahydrobis-demethoxycurcumin. In another related aspect, the hexahydrocurcuminoids further comprise of hexahydrocurcumin, hexahydro-demethoxycurcumin and hexahydrobis-demethoxycurcumin. In yet another preferred embodiment, octahydrocurcuminoids further comprise of octahydrocurcumin, octahydro-demethoxycurcumin and octahydrobis-demethoxycurcumin. In yet another related aspect, the therapeutic effect is brought about by decreasing collagen deposition, decreasing collagen 1A gene expression, reducing TGF-β levels, reducing oxidative stress and inflammation, reducing accumulation of Inflammatory cells in Bronchoalveolar lavage (BAL) fluids and inhibiting mast cell degranulation. In a further related aspect, the composition further comprises of stabilizing agents, bioavailability enhancers and antioxidants, pharmaceutically or nutraceutically or cosmeceutically accepted excipients and enhancers. In a preferred embodiment, the mammal is human.

In another preferred embodiment, the invention discloses a method for the inhibiting mast cell degranulation in mammals, said method comprising step of bringing into contact mast cells with a composition comprising 70%-80% w/w tetrahydrocurcuminoids, 10%-20% w/w hexahydrocurcuminoids and 5%-10% w/w octahydrocurcuminoids to bring about inhibition in histamine and cytokine release. In a related aspect, the tetrahydrocurcuminoids comprise of tetrahydrocurcumin, tetrahydro-demethoxycurcumin and tetrahydrobis-demethoxycurcumin. In another related aspect, the hexahydrocurcuminoids further comprise of hexahydrocurcumin, hexahydro-demethoxycurcumin and hexahydrobis-demethoxycurcumin. In yet another preferred embodiment, octahydrocurcuminoids further comprise of octahydrocurcumin, octahydro-demethoxycurcumin and octahydrobis-demethoxycurcumin. In a further related aspect, the composition further comprises of stabilizing agents, bioavailability enhancers and antioxidants, pharmaceutically or nutraceutically or cosmeceutically accepted excipients and enhancers. In a preferred embodiment, the mammal is human.

In another preferred embodiment, the invention discloses the use of a composition comprising 70%-80% w/w tetrahydrocurcuminoids, 10%-20% w/w hexahydrocurcuminoids and 5%-10% w/w octahydrocurcuminoids in inhibiting mast cell degranulation in mammals. In a related embodiment, the inhibition in mast cell degranulation is brought about by inhibiting histamine and cytokine release from mast cells. In a related aspect, the tetrahydrocurcuminoids comprise of tetrahydrocurcumin, tetrahydro-demethoxycurcumin and tetrahydrobis-demethoxycurcumin. In another related aspect, the hexahydrocurcuminoids further comprise of hexahydrocurcumin, hexahydro-demethoxycurcumin and hexahydrobis-demethoxycurcumin. In yet another preferred embodiment, octahydrocurcuminoids further comprise of octahydrocurcumin, octahydro-demethoxycurcumin and octahydrobis-demethoxycurcumin. In a further related aspect, the composition further comprises of stabilizing agents, bioavailability enhancers and antioxidants, pharmaceutically or nutraceutically or cosmeceutically accepted excipients and enhancers. In a preferred embodiment, the mammal is human.

In yet another related embodiment the bioavailability enhancer is selected from the group consisting of, but not limited to, piperine, quercetin, garlic extract, ginger extract, and naringin.

In another related aspect, one or more anti-oxidants and anti-inflammatory agents are selected from the group consisting of, but not limited to, vitamin A, D, E, K, C, B complex, rosmarinic acid, Alpha Lipoic Acid, Ellagic Acid, Glycyrrhizinic Acid, Epigallocatechin Gallate, plant polyphenols, Glabridin, moringa oil, oleanolic acid, Oleuropein, Carnosic acid, urocanic acid, phytoene, lipoid acid, lipoamide, ferritin, desferal, billirubin, billiverdin, melanins, ubiquinone, ubiquinol, ascorbyl palmitate, Mg ascorbyl phosphate, ascorbyl acetate, tocopherols and derivatives such as vitamin E acetate, uric acid, α-glucosylrutin, calalase and the superoxide dismutase, glutathione, selenium compounds, butylated hydroxyanisole (BHA), butylated hydroxytoluene (BHT), sodium metabisulfite (SMB), propyl gallate (PG) and amino acid cysteine.

Specific illustrative examples enunciating the most preferred embodiments are included herein below.

EXAMPLES

Example 1: Composition

The reductive metabolites of curcuminoids viz. tetrahydrocurcuminoids, hexahydrocurcuminoids and octahydrocurcuminoids are commonly biotransformed by the reductive enzymes and by hydrogenation (Mimura et. al., U.S. Pat. No. 5,266,344; Pan et al., Biotransformation of curcumin through reduction and glucuronidation in mice, Drug Metab Dispos, 1999, 27(1):486-494). They are also identified in nature and isolated from different plant sources (Majeed et al., Reductive Metabolites of Curcuminoids, Nutriscience Publishers LLC, 2019). Tetrahydrocurcumin along with its analogues tetrahydrodemethoxycurcumin, tetrahydrobisdemethoxycurcumin has been isolated from *Zingiber* sp. and *Curcuma* sp. (Peng et al., Chemical constituents of *Zingiber officinale* (Zingeberaceae). Yunnan Zhiwu Yanjiu, 2007; 29(1):125-128). Tetrahydrodemethoxycurcumin and tetrahydrobisdemethoxycurcumin has been reported to be present in the rhizome of Thai Zeodary (*Curcuma zedoaria*) (Matsuda et al., Anti-allergic principles from Thai zedoary: structural requirements of curcuminoids for inhibition of degranulation and effect on the release of TNF-alpha and IL4 in RBL-2H3 cells. Bioorg med hem, 2004; 12(22):5891-5898). Tetrahydrocurcumin is also obtained by biotransformation from curcumin (Shimoda et al., Formation of tetrahydrocurcumin by reduction of curcumin with cultured plant cells of Marchantia polymmrpha, Nat Prod Commun, 2012, 7(4):529-530).

Hexahydrocurcuminoids is also a naturally occurring plant metabolite found in the roots and rhizomes of *Curcuma, Zingiber* and *Alpina*. Hexahydrocurcuminoids have been isolated from rhizomes of fresh ginger (Peng et al., Cytotoxic, cytoprotective and antioxidant effects of isolated phenolic compounds from fresh ginger, Fitoterapia, 2012, 83(3):568-585). Hexahydrocurcuminoids are reported to occur in either of the two enatiomeric forms (S&R) and also as a racemic mixture (Majeed et al., Reductive Metabolites of Curcuminoids, Nutriscience Publishers LLC, 2019).

Similarly, Octahydrocurcuminoids are also isolated from the rhizomes of *C. xanthorrhiza* (Uehara et al., Diarylheptanoids from the rhizomes of *Curcuma xanthorrhiza* and *Alpina officinarum*, Chem Pharm Bull, 1987, 35(8):3298-3304). Octahydrocurcumin is also prepared by hydrogenation form tetrahydrocurcumin, in-vivo and microbial biotransformation (Majeed et al., Reductive Metabolites of Curcuminoids, Nutriscience Publishers LLC, 2019)

The composition claimed in the present invention was formulated using the following hydrogenation process:

Curcuminoids are reduced in solvent acetone under hydrogen pressure in the presence of Palladium/carbon at room temperature till the absence disappearance of the starting material. The product is isolated at off-white powder comprising Tetrahydrocurcumin, Tetrahydro demethoxycurcumin and Tetrahydro bisdemethoxycurcumin. Further, the tetrahydrocurcuminoids are reduced selectively to Hexahydrocurcuminoids in solvent ethanol under specific temperature and hydrogen pressure in the presence of Palladium/carbon till the disappearance of the starting material. The product is isolated as off-white powder comprising Hexahydrocurcuminoids and <5% of Octahydrocurcuminoids. For the preparation of octahydrocurcuminoids, Tetrahydrocurcuminoids are reduced to Octahydrocurcuminoids in solvent ethanol under high temperature and hydrogen pressure in the presence of Palladium/carbon till the complete conversion of the starting material. The product is isolated as off-white powder as essentially Octahydrocurcuminoids with traces of Hexahydrocurcuminoids.

The Tetrahydrocurcuminoids, Hexahydrocurcuminoids and Octahydrocurcuminoids are blended in the following proportion:

TABLE 1

Composition

| Content | Percentage (w/w) |
| --- | --- |
| Tetrahydrocurcuminoids | 70-80 |
| Hexahydrocurcuminoids | 10-20 |
| Octahydrocurcuminoids | 5-10 |

The composition is also available commercially as C3 Reduct® Special from Sami Labs Limited.

Example 2: Therapeutic Potential of the Composition Comprising Tetrahydrocurcuminoids, Hexahydrocurcuminoids and Octahydrocurcuminoids The therapeutic potential of the composition comprising Tetrahydrocurcuminoids, Hexahydrocurcuminoids and Octahydrocurcuminoids was tested by evaluating its ORAC and ROS & DPPH scavenging potential compared to curcuminoids and tetrahydrocurcuminoids.

Oxygen Radical Absorption Capacity Assay (ORAC):

Different concentrations of the standard (Trolox) (T5 to T1) or Test samples (S3 to S1), APPH (2,2'-Azobis (2-amidinopropane dihydrochloride) and Disodium fluorescein dye were added to a 96 well dark plate. Fluorescence reading was recorded after every 1 minute for 35 minutes at 485/520 nm (Fluostar Optima Microplate Reader) (f1 ... f35). The area under the curve (AUC) was calculated as, $$AUC = (1 + f1/f0 + f2/f0 + \ldots + f35/f0)$$

The net AUC was obtained by subtracting the AUC of the blank from that of the sample. The final ORAC values were expressed as micromoles of Trolox equivalents per liter or per gram of sample (µmol TE/g or µmol TE/L).

DPPH (2,2-Diphenyl-1-Picryl-Hydrazyl-Hydrate) Free Radical Assay

The test sample was dissolved in DMSO and diluted in 50% methanol for the assay. Different concentrations of compositions and individual actives were mixed with DPPH solution in methanol in a 96 well plate. The plate was incubated in the dark for 15 min, and the absorbance was measured at 540 nm using a microplate reader (TECAN Ltd, Männedorf, Switzerland). Blanks (DMSO, methanol) and standard (Trolox solution in DMSO) were recorded simultaneously.

The free radical scavenging activity was calculated as follows, $$\% \text{ scavenging activity} = (B-C) - (S-C)/(B-C) * 100$$

Where, B is the Absorbance of reference solution, C is the Absorbance of reference solution blank (Methanol only), S is the Absorbance of the test solution and C is the Absorbance of test solution blank. The sample was screened with variable concentrations to establish the inhibition concentration (IC50, the concentration reducing DPPH absorbance by 50%). The results are tabulated as table 2:

TABLE 2

ORAC and DPPH scavenging potential of the composition comprising tetrahydrocurcuminoids, hexahydrocurcuminoids and octahydrocurcumioids (THO Composition)

| Compound | ORAC value µmole Trolox/g | DPPH - $IC_{50}$ µg/ml |
| --- | --- | --- |
| Curcuminoids | 10115.92 ± 733.3 | 3.34 |
| Tetrahydrocurcuminoids | 11259.21 ± 642.73 | 2.7 |
| Hexahydrocurcuminoids | 11418.45 ± 626.7 | 2.24 |
| Octahydrocurcuminoids | 11335.98 ± 978.13 | 2.71 |
| THO Composition | 12114.5 ± 797.1 | 2.46 |

The results revealed that the composition comprising tetrahydrocurcuminoids, hexahydrocurcuminoids and octahydrocurcuminoids showed better ORAC and DPPH scavenging compared to curcuminoids and tetrahydrocurcuminoids, indicating higher therapeutic efficacy of the composition. Further therapeutic activities were evaluated for the composition per se.

Intracellular Reactive Oxygen Species (ROS) Assay

Swiss 3T3 (5×104 cells/well) cells were seeded in 96 well black microplates and allowed to grow overnight. Cells were induced with H2O2 (25 mM) with or without different concentrations of sample in DMEM 1% FBS for four hours. Freshly prepared DCFH-DA reagent was added to all the wells at a concentration of 10 µg/well and incubated at 37° C. for 30 mins. The fluorescence was recorded at a wavelength of 485:520 (Ex:Em) nm in BMG Fluo Star Optima microplate reader. The percentage of ROS scavenging was calculated with respect to the fluorescence intensity of H2O2 treated control cells.

Figure 1:
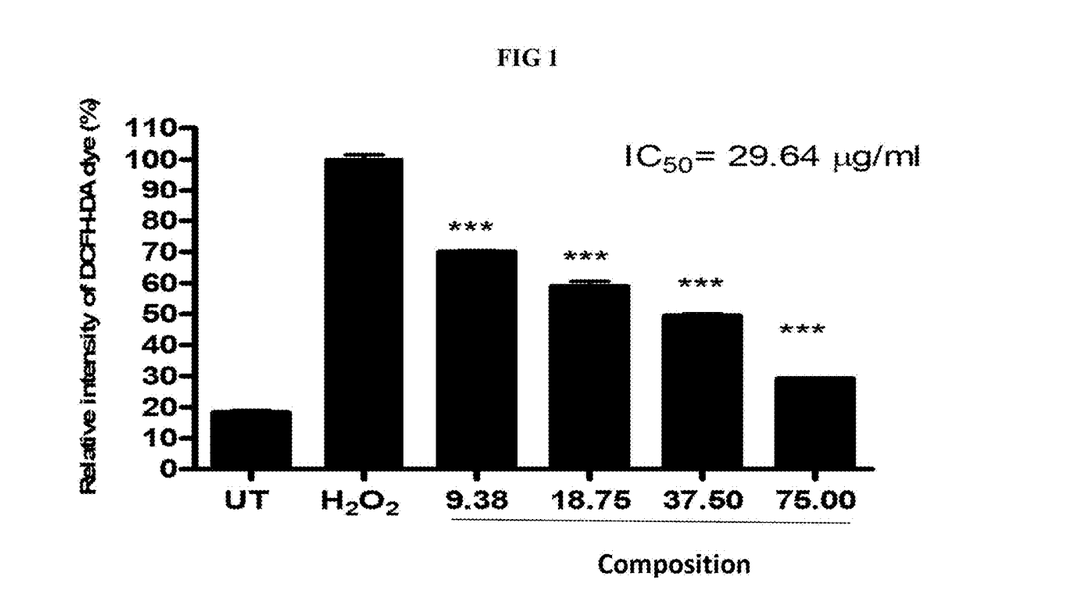
FIG. 1 is a graphical representation showing the reduction in ROS in fibroblast cells treated with a composition comprising tetrahydrocurcuminoids hexahydrocurcuminoids and octahydrocurcuminoids. ***, $P<0.001$

The results (FIG. 1) indicated that the composition was very effective in reducing the ROS in fibroblast cells with an IC50 of 29.64 µg/mL.

Example 3—Lung Fibrosis—Invitro Assays

The potential of the composition in managing lung fibrosis and inhibiting mast cell degranulation was tested by the following invitro assays:

Mast cells play an important role in managing and triggering inflammatory and immediate allergic reactions. They release a variety of inflammatory mediators, such as histamine, proteases, chemotactic factors, cytokines and metabolites of arachidonic acid that act on the vasculature, smooth muscle, connective tissue, mucous glands and inflammatory cells (Amin K, The role of mast cells in allergic inflammation, Respiratory Medicine, 2012; 106; 9-14). It is reported that Mast cell numbers in the lung of patients with fibrotic lung disease are increased compared to control subjects and is positively correlated with the severity of fibrosis. In addition, histamine concentrations in the BAL fluid of patients with IPF are elevated about 10-fold that of control subjects (Cruse et al., Mast cells in airway diseases and interstitial lung disease, Eur J Pharmacol. 2016; 778: 125-138). Thus it is imperative to inhibit mast cell degranulation in subjects with ILD.

The composition was tested for its ability to prevent histamine and cytokine release in mast cells.

Histamine Release Assay

P815 cells were purchased from the American Type Culture Collection (ATCC, Manassas, Va., USA) and cultured in Dulbecco's minimal essential medium (Gibco, UK) supplemented with 10% (v/v) heat-inactivated fetal bovine serum (FBS, Gibco, UK) and maintained in a 5% C02 incubator at 37° C. When the cells were 80% confluence, they were harvested, resuspended in fresh medium, and seeded 5×105 cells per well in 24-well plates for the experiments.

After cells washed with ice cold HEPES buffered Tyrode's solution containing 0.1% bovine serum albumin without Ca++ and Mg++ (composed of 137 mmol/L NaCl, 5.6 mmol/L glucose, 2.7 mmol/L KCl, 0.4 mmol/L $NaH_2PO_4$, and 10 mmol/L HEPES [pH 7.4]), the cells were treated different concentration of composition along with 30 g of compound 48/80. After 3 hr of incubation the plate was kept over ice for 10 minutes to terminate the degranulation. Then the supernatant was collected after centrifugation at 5000 rpm for 5 minutes. To the 50 µL of supernatant, 50 µL of 4N NaOH and 10 µL of opthaldialdehyde (10 mg/mL) was added and incubate in dark at room temperature for 10 minutes. Then the reaction was stopped with 50 µL of N HCl and the fluorescence was recorded at 390/460 ex/em. The percentage of histamine release was calculated with respect to the fluorescence intensity of compound 48/80 treated control cells.

Figure 2:
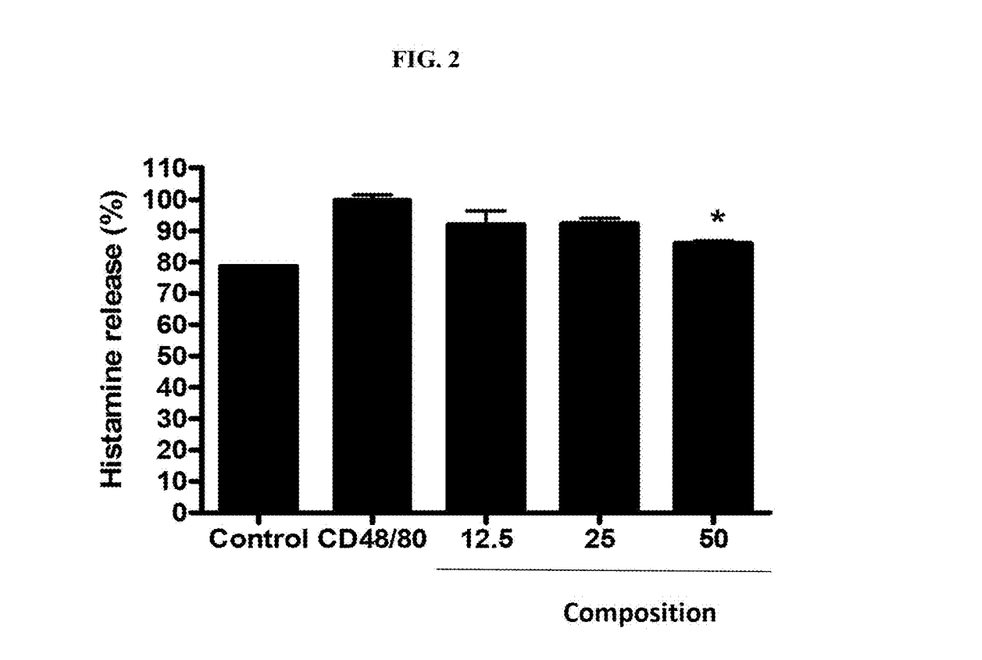
FIG. 2 is a graphical representation showing the reduction in histamine release by mast cells treated with a composition comprising tetrahydrocurcuminoids hexahydrocurcuminoids and octahydrocurcuminoids.

The results (FIG. 2) indicated that 50 µg/mL of the composition was effective in reducing the histamine release in the supernatant of mast cell.

In Vitro Lung Inflammation Assay

A549 (1×104 cells/well) cells were seeded in 96 well microplates and allowed to grow overnight. After overnight serum starvation, cells were pre-treated with IL1β (5 ng/mL) with or without different concentrations of composition for 4 hr in 1% FBS RPMI 1% FBS medium. Further the cells were treated with sample alone for 24 hr. After 24 hr the supernatant was collected for determining level of IL6 by ELISA (R&D Systems, Minneapolis, Minn., USA) as per the manufacturer's instructions. The percentage inhibition of IL6 was calculated with respect to IL1β treated control.

Figure 3:
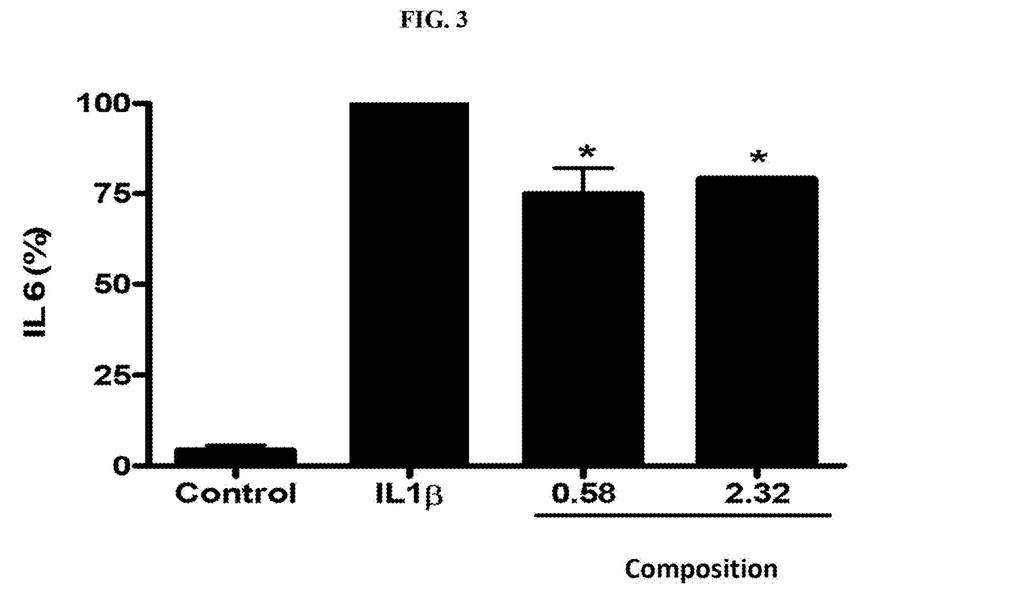
FIG. 3 is a graphical representation showing the reduction in IL 6 in the supernatant of lung epithelial cells (A549) cells induced with IL1 β, by the composition comprising tetrahydrocurcuminoids hexahydrocurcuminoids and octahydrocurcuminoids. *indicate $P<0.05$

The composition was effective in reducing the level of IL 6 (a inflammatory cytokine) in the supernatant of A549 cells induced with IL1 β (FIG. 3)

The composition was very effective in preventing histamine release and inhibit mast cell degranulation and thus could be used in treating different forms of allergies.

Example 4—In Vivo Study for Lung Fibrosis

The protocol followed for animal experiments was approved by the institutional animal ethics committee as per the Committee for the Purpose of Control and Supervision of Experiments on Animals (CPCSEA), India in compliance with Government of India guidelines and conform to the Guide for the Care and Use of Laboratory Animals published by the National Institutes of Health (NIH Publication, 8th Edition, 2011). A total of 40 C57/BL6 mice (aged 6-8 weeks) were randomly divided into five groups (mean body weight 20-22 g) of eight mice each. Animals were housed under standard laboratory conditions (temperature 23.5° C., humidity=58-64%), with 12 h light and 12 h dark cycle, fed with normal diet and water ad libitum.

To generate a pulmonary fibrosis model, experimental mice were administered a single dose of 5 mg/kg body weight Bleomycin by Intratracheal instillation, and control mice received saline. For the therapeutic treatment, from day 3 mice received C3R blend by oral gavages (20, 40 and 80 mg/kg) for a period of three week after bleomycin intratracheal administration. At the end of the experimental period, the animals were humanely sacrificed, organs, tissues, and blood were collected for further analysis. Bodyweight and organ weight were recorded for all animals. Lungs were dissected out, weighed, and stored in RNA later or OCT for histological analysis Antioxidant and Anti-Inflammatory Effects Bronchoalveolar Lavage (BAL).

BAL fluid (BALF) was collected by intratracheal instillation of 5 ml of sterile saline into the lungs. Whole BALF was then centrifuged at 1500 rpm for 5 min. After centrifugation, the residual suspension was analysed to determine the total cell, neutrophil, eosinophil, and lymphocyte counts using a haematology analyser.

Figure 4:
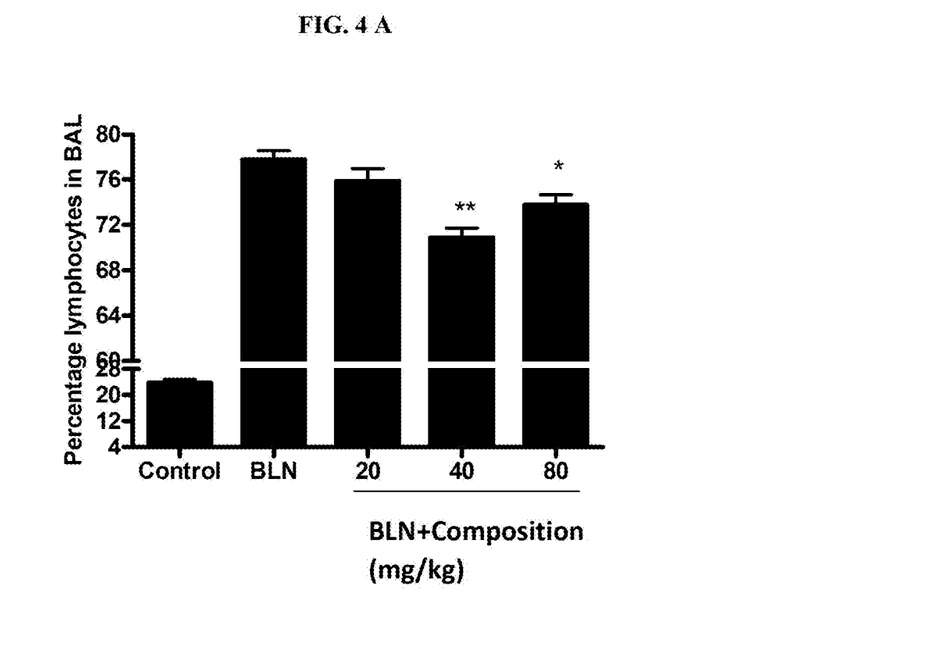
FIG. 4A is a graphical representation showing the reduction in accumulation of inflammatory cells observed in lymphocytes using a composition comprising tetrahydrocurcuminoids hexahydrocurcuminoids and octahydrocurcuminoids. *indicate $P<0.001$
FIG. 4B is a graphical representation showing the reduction in accumulation of inflammatory cells observed in eiosinophils using a composition comprising tetrahydrocurcuminoids hexahydrocurcuminoids and octahydrocurcuminoids. *indicate $P<0.001$

Reduction in accumulation of inflammatory cells observed in BAL in treated animals in both lymphocytes (FIG. 4A) and Eiosinophils (FIG. 4B)

Similarly, IL-6 and IFN-γ levels were estimated using standard procedures. RNA was extracted from lung sample using the trizol method. The Lung tissues were homogenized in liquid nitrogen followed by trizol extraction and DNAse to remove any traces of DNA. First-strand cDNA was prepared from RNA samples using oligodT primers and Superscript III reverse transcriptase (cDNA synthesis kit, Invitrogen™). Quantitative real-time PCR (qRT-PCR) was performed with SYBR Green I fluorescent dye using Light cycler 96 according to the manufacturer's instructions (Light Cycler® FastStart DNA Master SYBR Green I, Roche). The primers used for the analysis are provided in Table 3. The 18s gene was used as the housekeeping gene. The gene expression of the target gene in each test sample was determined by relative quantification using the comparative Ct (ΔΔCt) method.

TABLE 3

List of Primers for IL-6 and IFN-γ expression

| Sl No | Oligo Name | Sequence 5' to 3' | Length |
|---|---|---|---|
| 1 | m IL6 F | GGCCTTCCCTACTTCACAAG | 20 |
|   | m IL6 R | ATTTCCACGATTTCCCAGAG | 20 |
| 2 | m IFN F | TGAACGCTACACACTGCATCTTGG | 24 |
|   | m IFN R | CGACTCCTTTTCCGCTTCCTGAG | 23 |
| 3 | m 18s F | CGCCGCTAGAGGTGAAATTCT | 21 |
|   | m 18s R | CGAACCTCCGACTTTCGTTCT | 21 |

Figure 5:
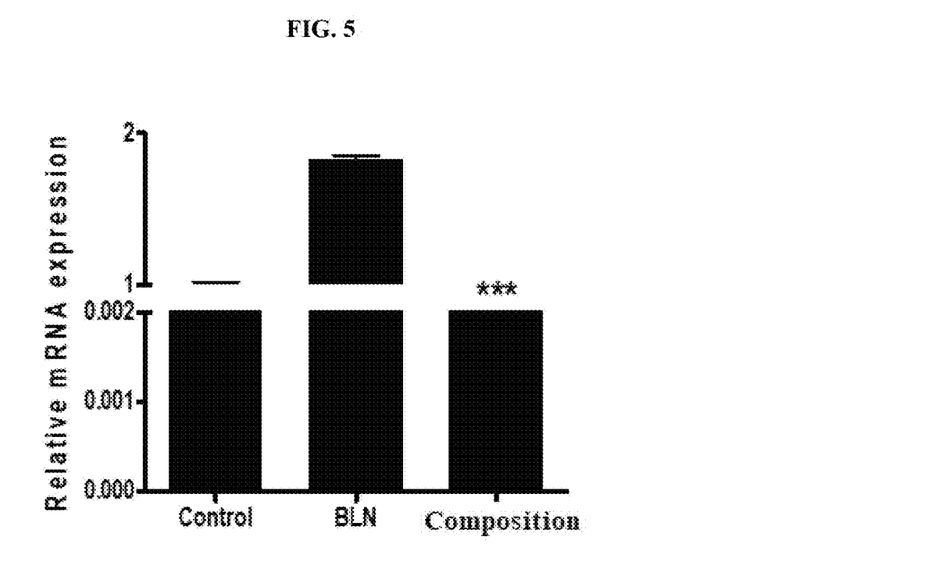
FIG. 5 is a graphical representation showing the relative gene expression of IL 6 in lung lysate of animals treated with a composition comprising tetrahydrocurcuminoids hexahydrocurcuminoids and octahydrocurcuminoids. *indicate $P<0.001$
Figure 6:
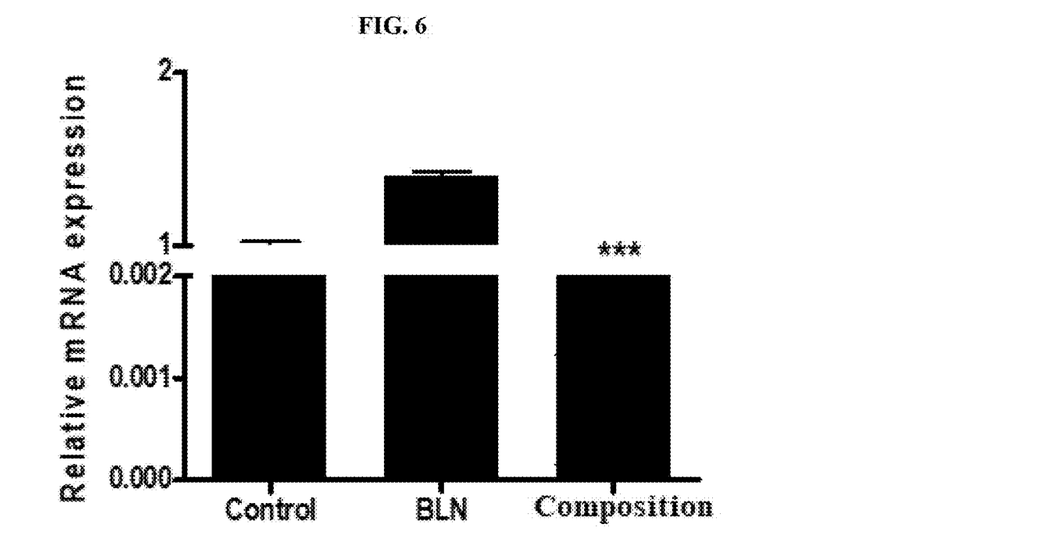
FIG. 6 is a graphical representation showing the relative gene expression of IFN-γ in lung lysate of animals treated with a composition comprising tetrahydrocurcuminoids hexahydrocurcuminoids and octahydrocurcuminoids. *indicate $P<0.001$

The composition was effective in reducing relative gene expression of IL 6 (FIG. 5) and IFN-γ (FIG. 6) in the Lung lysate in compared to Bleomycin group

MDA

Malondialdehyde, a lipid peroxidation end product in tissue homogenate, was determined according to the method of Beuge and Aust., 1978 with some modifications. The tissue homogenate was mixed with an equal volume of TBA-TCA-HCl solution (0.5% TBA, 20% TCA and 0.25 N HCl). The mixture was heated for 30 min in a boiling water bath (95-100° C.) and cooled immediately. The tubes were centrifuged at 10,000 rpm for 10 min and absorbance of the supernatant was read at 532 nm. The level of lipid peroxides was expressed as μM MDA formed/mg protein.

Figure 7:
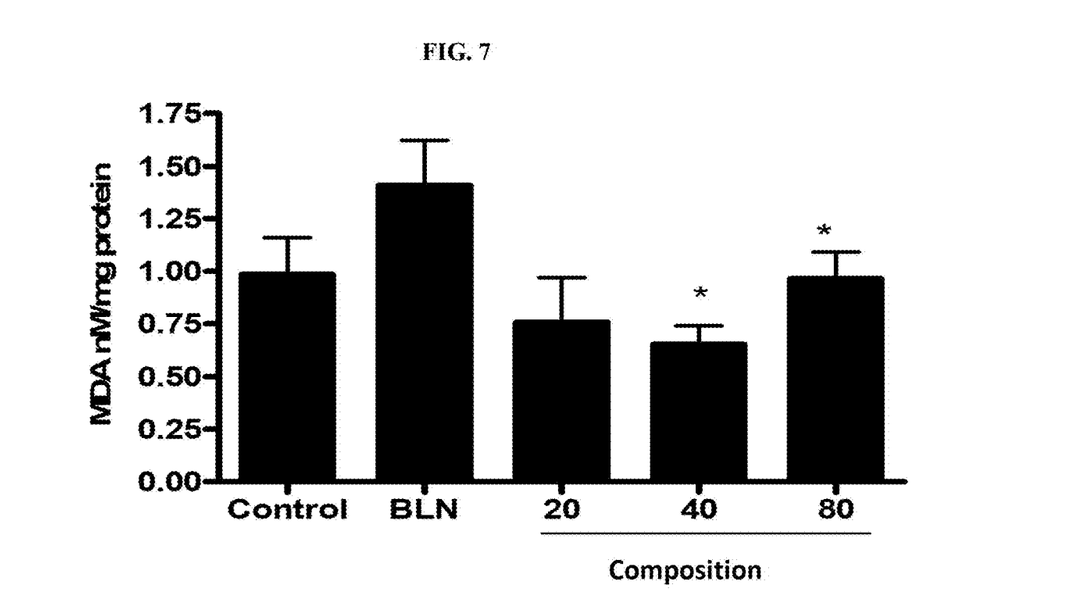
FIG. 7 is a graphical representation showing the reduction in lung MDA levels in animals treated with a composition comprising tetrahydrocurcuminoids hexahydrocurcuminoids and octahydrocurcuminoids. *indicate $P<0.05$

The MDA levels were significantly reduced in the group treated with the composition (FIG. 7)

SOD

Super oxide dismutase (SOD), an antioxidant enzyme that catalyzes the dismutation of superoxide into hydrogen peroxide and oxygen. It protects the lung from oxidative damage that results in diseases such as pulmonary fibrosis The activity of SOD was measured by WST-1 method using a kit as per the manufacturer's instructions (Elabsciences). Xanthine Oxidase (XO) catalyzes the reaction of WST-1 with O2- to generate a water-soluble formazan dye. SOD catalyzes the disproportionation of superoxide anions. The activity of SOD is negatively correlated with the amount of formazan dye.

Figure 8:
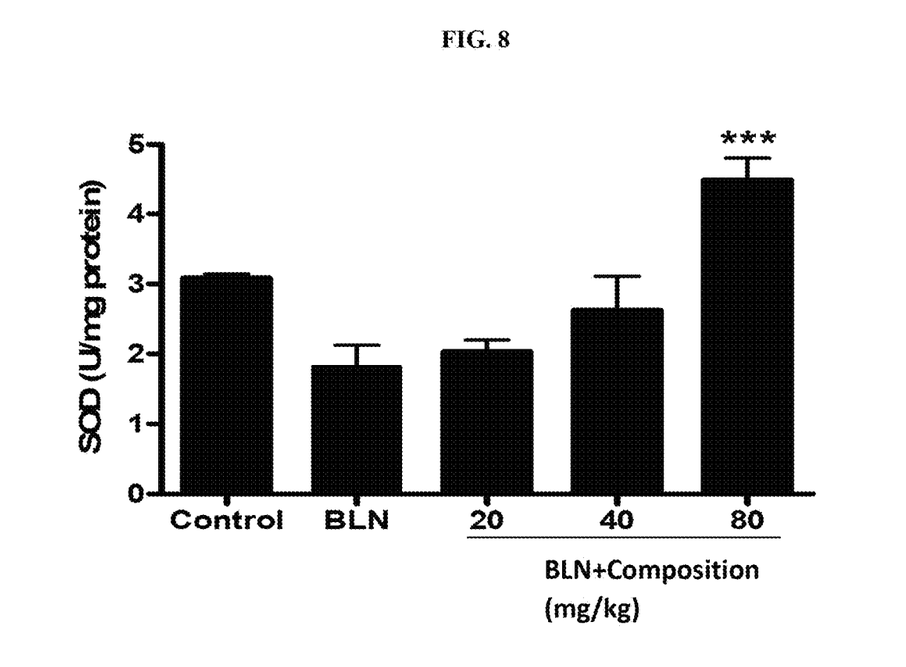
FIG. 8 is a graphical representation showing the increase in SOD activity in lung lysate of animals treated with a composition comprising tetrahydrocurcuminoids hexahydrocurcuminoids and octahydrocurcuminoids. ***indicate $P<0.001$

The composition significantly increase the activity of SOD (FIG. 8).

Nrf2 Expression

Nuclear factor erythroid 2 related factor 2 (Nrf2), a key regulator of antioxidant defense system, protects cells against oxidative stress.

Frozen lung from the animals were homogenized and the cells were lysed using ice-cold RIPA buffer containing protease (1× protease inhibitor cocktail–HI media) and phosphatase (sodium orthovanadate 1 mM). Protein concentration was estimated by the BCA method (G-Biosciences, USA). Cellular protein (100 μg) was loaded per lane in denatured 10% polyacrylamide gel (SDS-PAGE). The separated proteins were transferred to a polyvinylidenedifluoride membrane (Invitrolon™ PVDF, Thermo Fisher Scientific, USA) and blocked in 5% nonfat dry milk for 2 hours. Membranes were then incubated with the appropriate dilutions of anti-mouse primary antibodies at 4° C. for 18 hours, followed by horseradish peroxidase-conjugated secondary antibody (Thermo Scientific, USA) for 2 hours at 37° C. Immunoreactive protein bands were detected by ECL ((Pierce ECL plus, Thermo Scientific, USA). Immunoblots were quantified using Image J software (version 1.52a, National Institute of Health, USA). Table 4 lists the antibodies used for the experiments

TABLE 4

List of Antibodies

| Antibody | Code | Source |
|---|---|---|
| NFE2L2 Antibody 100 ug/ml (NRF2) | CSB-PA003481 | Cusabio |
| Beta Actin | 4967 | Cell signalling |

Figure 9:
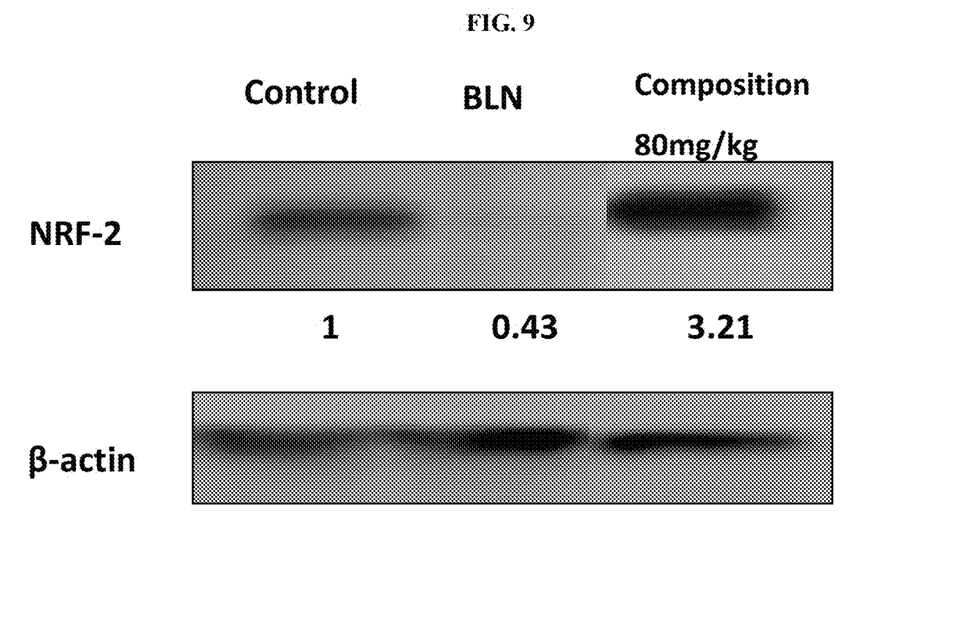
FIG. 9 is a western blot image showing the increase in expression of NRF-2 protein in lung lysates of animals treated with a composition comprising tetrahydrocurcuminoidshexahydrocurcuminoidsandoctahydrocurcuminoids.

The composition was effective in recovering NRF-2 (a protein which regulates the antioxidant enzymes to prevent the tissues from oxidative damage) expression in the Lung lysate in compare to Bleomycin induced group (FIG. 9)

TGF-Beta Expression

The TGF-β pathway play a pivotal role in lung fibrosis. It induces secretion of growth factors that facilitate the proliferation of connective tissues, facilitates Epithelial-mesenchymal transition (EMT) in alveolar cells and regulated metalloproteinase activity and tissue remodelling. Inhibition of TGF-β is approved clinical treatments for Idiopathic pulmonary fibrosis (IPF) (E.g Pirfenidone)

Figure 10:
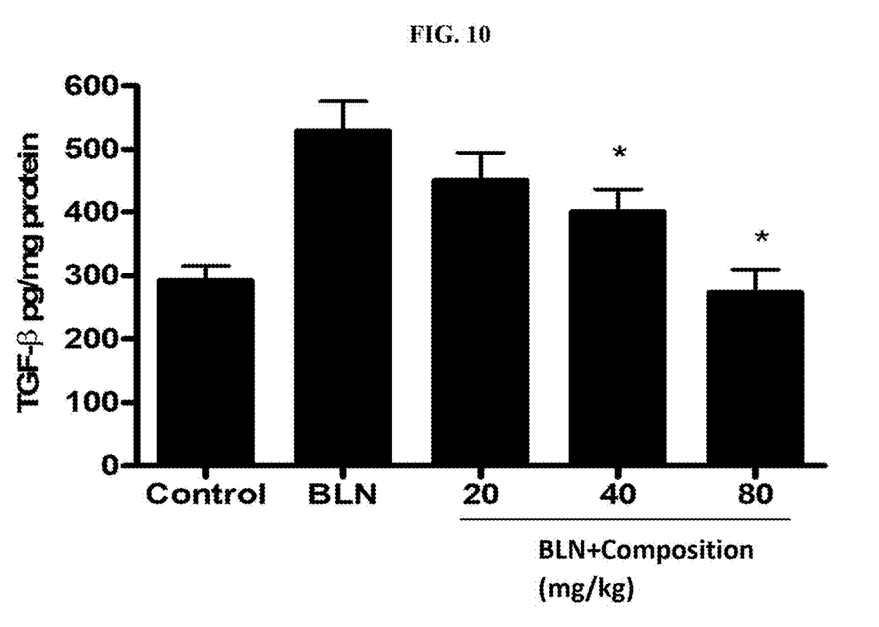
FIG. 10 is a graphical representation showing the reduction in TGF-β expression in the lung lysates of animals treated with a composition comprising tetrahydrocurcuminoids hexahydrocurcuminoids and octahydrocurcuminoids. *indicate $P<0.05$

In the present invention, the concentration of TGF-β in lung homogenate was carried out by ELISA (R&D Systems (Minneapolis, Minn., USA) as per the manufacturer's instructions. The results were expressed as concentration per mg protein for lung homogenate. The composition was effective in reducing the concentration of TGF-β in the lung homogenate at 40 and 80 mg/kg bodyweight (FIG. 10)

Histological Analyses

For Hematoxylin and Eosin staining, sections were cut from paraffin blocks of lung tissue prefixed in Bouin's solution and stained with Lillie-Mayer's Hematoxylin (Muto Pure Chemicals Co., Ltd., Japan) and eosin solution (Wako Pure Chemical Industries). To visualize collagen deposition, Bouin's fixed lung sections were stained using a picrosirius red solution (Waldeck, Germany). For quantitative analysis of fibrosis area, bright field images of Sirius red-stained sections and images were captured using the Bright field microscope (Nikon Eclipse), and the positive areas in 5 fields/section were measured using ImageJ software (National Institute of Health, USA).

Figure 11:
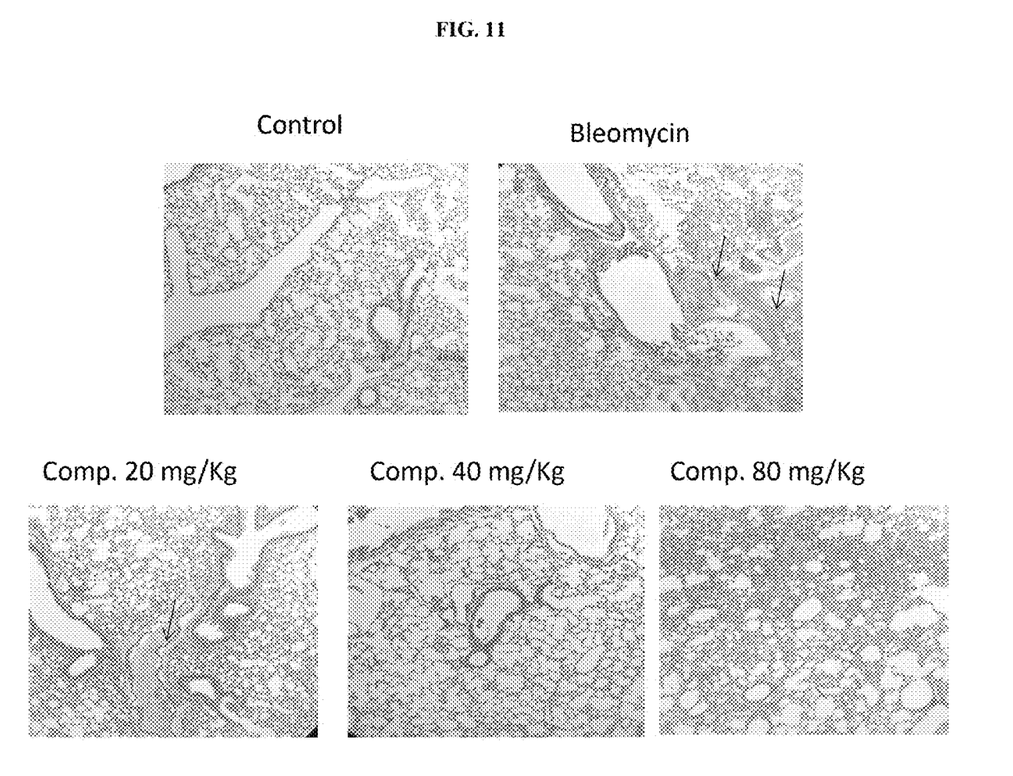
FIG. 11 is a histopathological image of the lung section showing the reduction in lung inflammation in animals treated with a composition comprising tetrahydrocurcuminoids hexahydrocurcuminoids and octahydrocurcuminoids.
Figure 12:
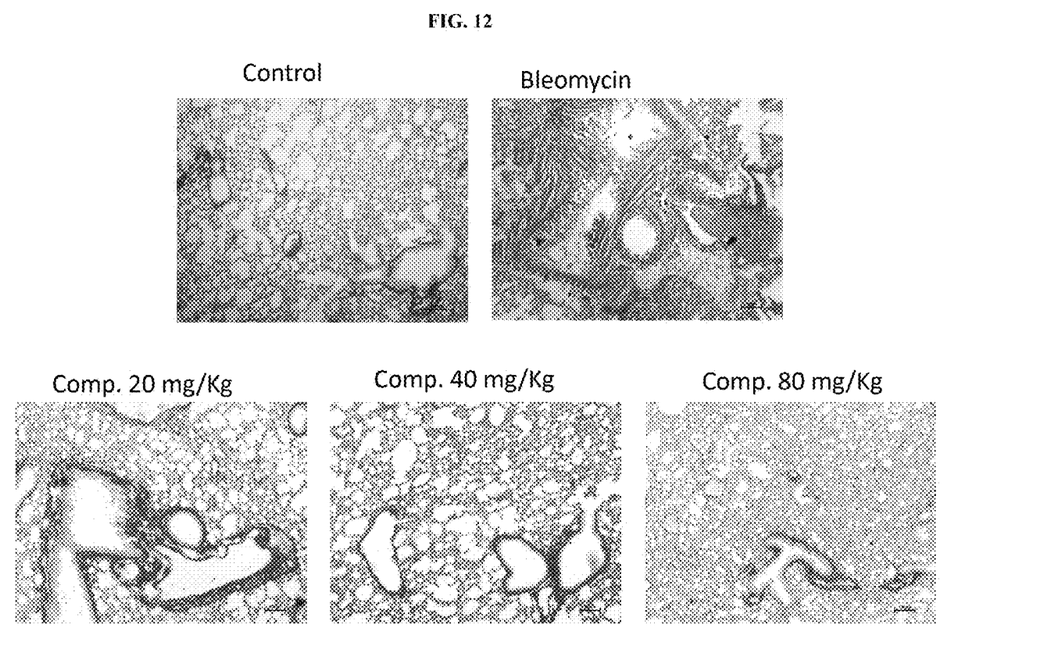
FIG. 12 is a histopathological image of the lung section showing the reduction in collage deposition in animals treated with a composition comprising tetrahydrocurcuminoids hexahydrocurcuminoids and octahydrocurcuminoids.
Figure 13:
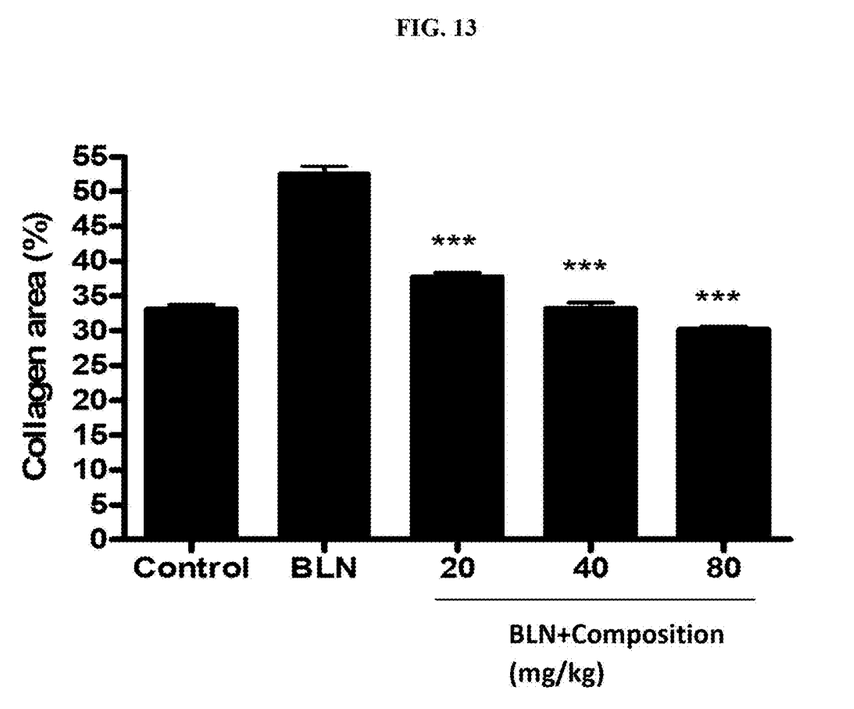
FIG. 13 is a graphical representation showing the reduction in collagen deposition in lungs of animals treated with a composition comprising tetrahydrocurcuminoids hexahydrocurcuminoids and octahydrocurcuminoids. ***indicate $P<0.001$

Significant reduction in lung inflammation was observed in the histopathogical analysis (FIG. 11). Collagen deposition at alveolar of the Lung tissue was also significantly reduced in the group administered with the composition (FIG. 12 and FIG. 13)

The collagen 1 A gene expression was also estimated using quantitative RT-PCR. RNA was extracted from lung sample using the trizol method. The Lung tissues were homogenized in liquid nitrogen followed by trizol extraction and DNAse to remove any traces of DNA. First-strand cDNA was prepared from RNA samples using oligodT primers and Superscript III reverse transcriptase (cDNA synthesis kit, Invitrogen™). Quantitative real-time PCR (qRT-PCR) was performed with SYBR Green I fluorescent dye using Light cycler 96 according to the manufacturer's instructions (Light Cycler® FastStart DNA Master SYBR Green I, Roche). The primers used for the analysis are provided in Table 5. The 18s gene was used as the housekeeping gene. The gene expression of the target gene in each test sample was determined by relative quantification using the comparative Ct (ΔΔCt) method.

TABLE 5

List of primers

| Si No | Oligo Name | Sequence 5' to 3' | Length |
|---|---|---|---|
| 1 | m Cola1 F | TTCCCTGGACCTAAGGGTACT | 21 |
|   | m Cola1 R | TTGAGCTCCAGCTTCGCC | 18 |
| 2 | m 18s F | CGCCGCTAGAGGTGAAATTCT | 21 |
|   | m 18s R | CGAACCTCCGACTTTCGTTCT | 21 |

Figure 14:
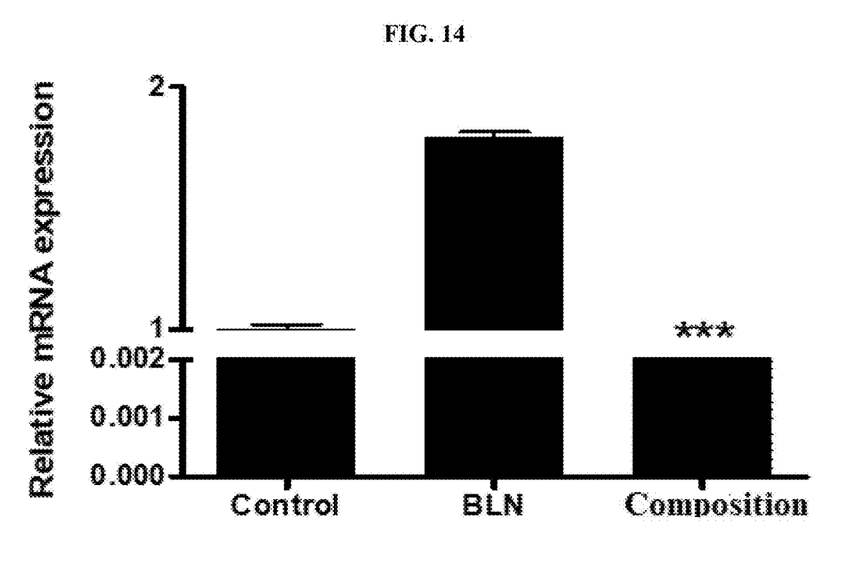
FIG. 14 is a graphical representation showing the decrease in gene expression of Col −1A in lung lysates of animals treated with a composition comprising tetrahydrocurcuminoidshexahydrocurcuminoidsandoctahydrocurcuminoids.

The composition was effective in reducing relative gene expression of Col-1A (type I collagen found in connective tissues) in the Lung lysate in compare to Bleomycin induced group (FIG. 14).

Overall, the composition comprising tetrahydrocurcuminoids, hexahydrocurcuminoids and octahydrocurcuminoids was effective in reducing markers of fibrosis and inflammation in bleomycin induced pulmonary and fibrosis in mice. It can reduce histamine release from Mast cells suggesting an anti-allergy activity. The composition is very suitable as a supplement for the management of respiratory diseases including ILD and SARS-CoV-2 induced acute respiratory syndrome.

While the invention has been described with reference to a preferred embodiment, it is to be clearly understood by those skilled in the art that the invention is not limited thereto. Rather, the scope of the invention is to be interpreted only in conjunction with the appended claims.

We claim:

1. A method for the therapeutic management or interstitial king disease in mammals, said method comprising step of administering a composition comprising 70%-80% w/w tetrahydrocurcuminoids, 10-20% w/w hexahydrocurcuminoids and 5%-10% w/w octahydrocurcuminoids to mammals in need of such therapeutic management.

2. The method as in claim 1, wherein the tetrahydrocurcuminoids comprise of tetrahydrocurcumin, tetrahydrodemethoxycurcumin and tetrahydrobis-demethoxycurcumin.

3. The method as in claim 1, wherein the hexahydrocurcuminoids comprise of hexahydrocurcumin, hexahydrodemethoxycurcumin and hexahydrobis-demethoxycurcumin.

4. The method as in claim 1, wherein octahydrocurcuminoids further comprise of octahydrocurcumin, octahydrodemethoxycurcumin and octahydrobis-demethoxycurcumin.

5. The method as in claim 1, wherein the therapeutic effect is decreasing collagen deposition, decreasing collagen 1A gene expression, reducing TGF-β levels, reducing oxidative stress and inflammation, reducing accumulation of Inflammatory cells in Bronchoalveolar lavage (BAL) fluids and inhibiting mast cell degranulation.

6. The method as in claim 1, wherein the composition further comprises of stabilizing agents, bioavailability enhancers and antioxidants, pharmaceutically or nutraceutically or cosmeceutically accepted excipients and enhancers.

7. The method as in claim 1, wherein the mammal is human.

8. A method for inhibiting mast cell degranulation in a mammal having interstitial lung disease, said method comprising administering to the mammal a composition comprising 70%-80% w/w tetrahydrocurcuminoids, 10%-20% w/w hexahydrocurcuminoids and 5%-10% w/w octahydrocurcuminoids to bring about inhibition in histamine and cytokine release.

9. The method as in claim 8, wherein the tetrahydrocurcuminoids comprise of tetrahydrocurcumin, tetrahydrodemethoxycurcumin and tetrahydrobis-demethoxycurcumin.

10. The method as in claim 8, wherein the hexahydrocurcuminoids further comprise of hexahydrocurcumin, hexahydro-demethoxycurcumin and hexahydrobis-demethoxycurcumin.

11. The method as in claim 8, wherein octahydrocurcuminoids further comprise of octahydrocurcumin, octahydrodemethoxycurcumin and octahydrobis-demethoxycurcumin.

12. The method as in claim 8, wherein the composition further comprises of stabilizing agents, bioavailability enhancers and antioxidants, pharmaceutically or nutraceutically or cosmeceutically accepted excipients and enhancers.

13. The method as in claim 8, wherein the mammal is human.

* * * * *

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Forward Primer of m Cola1

<400> SEQUENCE: 1
ttccctggac ctaagggtac t                                       21

<210> SEQ ID NO 2
<211> LENGTH: 18
<212> TYPE: DNA
<213> ORGANISM: Artificial Sequence
<220> FEATURE:
<223> OTHER INFORMATION: Reverse Primer of m Cola1

<400> SEQUENCE: 2
ttgagctcca gcttcgcc                                           18

<210> SEQ ID NO 3
<211> LENGTH: 20
<212> TYPE: DNA
<213> ORGANISM: Artificial Sequence
<220> FEATURE:
<223> OTHER INFORMATION: Forward Primer for IL6

<400> SEQUENCE: 3
ggccttccct acttcacaag                                         20

<210> SEQ ID NO 4
<211> LENGTH: 20
<212> TYPE: DNA
<213> ORGANISM: Artificial Sequence
<220> FEATURE:
<223> OTHER INFORMATION: Reverse primer for IL6

<400> SEQUENCE: 4
atttccacga tttcccagag                                         20

<210> SEQ ID NO 5
<211> LENGTH: 24
<212> TYPE: DNA
<213> ORGANISM: Artificial Sequence
<220> FEATURE:
<223> OTHER INFORMATION: Forward Primer for IFN-gamma

<400> SEQUENCE: 5
```

```
tgaacgctac acactgcatc ttgg                                              24

<210> SEQ ID NO 6
<211> LENGTH: 23
<212> TYPE: DNA
<213> ORGANISM: Artificial Sequence
<220> FEATURE:
<223> OTHER INFORMATION: Reverse Primer for IFN-gamma

<400> SEQUENCE: 6
cgactccttt tccgcttcct gag                                               23

<210> SEQ ID NO 7
<211> LENGTH: 21
<212> TYPE: DNA
<213> ORGANISM: Artificial Sequence
<220> FEATURE:
<223> OTHER INFORMATION: Forward Primer for 18s rRNA

<400> SEQUENCE: 7
cgccgctaga ggtgaaattc t                                                 21

<210> SEQ ID NO 8
<211> LENGTH: 21
<212> TYPE: DNA
<213> ORGANISM: Artificial Sequence
<220> FEATURE:
<223> OTHER INFORMATION: Reverse Primer for 18s rRNA

<400> SEQUENCE: 8
cgaacctccg actttcgttc t                                                 21
```

UNITED STATES PATENT AND TRADEMARK OFFICE
CERTIFICATE OF CORRECTION

| | |
|---|---|
| PATENT NO. | : 11,491,119 B2 |
| APPLICATION NO. | : 17/071682 |
| DATED | : November 8, 2022 |
| INVENTOR(S) | : Muhammed Majeed et al. |

It is certified that error appears in the above-identified patent and that said Letters Patent is hereby corrected as shown below:

In the Claims

Claim 1 Should read:
1. A method for the therapeutic management or interstitial lung disease in mammals, said method comprising step of administering a composition comprising 70%-80% w/w tetrahydrocurcuminoids, 10-20% w/w hexahydrocurcuminoids and 5%-10% w/w octahydrocurcuminoids to mammals in need of such therapeutic management.

Signed and Sealed this
Fourteenth Day of February, 2023

*Katherine Kelly Vidal*
Katherine Kelly Vidal
*Director of the United States Patent and Trademark Office*